(12) United States Patent  
Sutter et al.

(10) Patent No.: US 8,454,601 B2
(45) Date of Patent: Jun. 4, 2013

(54) BIPOLAR COAGULATION ELECTRODES

(75) Inventors: Hermann Sutter, Gundelfingen (DE); Dirk Weitkamp, Waldkirch (DE)

(73) Assignee: Sutter Medizintechnik GmbH, Freiburg (DE)

( * ) Notice: Subject to any disclaimer, the term of this patent is extended or adjusted under 35 U.S.C. 154(b) by 1332 days.

(21) Appl. No.: 11/083,766

(22) Filed: Mar. 18, 2005

(65) Prior Publication Data

US 2005/0222602 A1 Oct. 6, 2005

(30) Foreign Application Priority Data

Mar. 19, 2004 (DE) .......................... 10 2004 013 530

(51) Int. Cl.
*A61B 18/12* (2006.01)
*A61B 17/28* (2006.01)

(52) U.S. Cl.
USPC ........................................... 606/51; 606/205

(58) Field of Classification Search
USPC ................. 606/205–208, 40, 41, 45–52, 151, 606/170
See application file for complete search history.

(56) References Cited

U.S. PATENT DOCUMENTS

| 4,049,002 | A | | 9/1977 | Kletschka et al. | |
|---|---|---|---|---|---|
| 5,352,223 | A | * | 10/1994 | McBrayer et al. | 606/51 |
| 5,395,369 | A | | 3/1995 | McBrayer et al. | |
| 5,626,609 | A | * | 5/1997 | Zvenyatsky et al. | 606/208 |
| 5,697,949 | A | | 12/1997 | Giurtino et al. | |
| 5,853,412 | A | | 12/1998 | Mayenberger | |
| 6,309,404 | B1 | * | 10/2001 | Krzyzanowski | 606/208 |
| 6,440,085 | B1 | * | 8/2002 | Krzyzanowski | 600/564 |
| 6,458,129 | B2 | * | 10/2002 | Scarfi | 606/50 |
| 6,669,696 | B2 | * | 12/2003 | Bacher et al. | 606/51 |
| 2002/0183784 | A1 | * | 12/2002 | Lutze et al. | 606/206 |
| 2003/0139741 | A1 | * | 7/2003 | Goble et al. | 606/48 |

FOREIGN PATENT DOCUMENTS

| EP | 0 316 816 | 6/1993 |
|---|---|---|
| FR | 2 469 912 | 11/1979 |

* cited by examiner

*Primary Examiner* — Kathleen Holwerda
(74) *Attorney, Agent, or Firm* — Volpe and Koenig, P.C.

(57) ABSTRACT

A bipolar coagulation forceps (1) with a fixed forceps leg (2), a pivot support (3), and a pivoting forceps leg (4), which can pivot relative to the fixed forceps leg via a pivot element (6, 11, 12) and which is electrically insulated from the fixed forceps leg is provided, with the forceps legs (2, 4) essentially being made from biocompatible metal. The pivot element (6, 11, 12) is likewise essentially made from biocompatible metal and attaches directly to the moving forceps leg (4). An insulating body (5a, 5b) electrically insulating the pivot element (6, 11, 12) and the moving forceps leg (4) from the fixed forceps leg (2) is arranged on or fixed to the fixed forceps leg (2) as a pivot support (3), on which the moving forceps leg (4) is supported by the pivot element (6, 11, 12).

12 Claims, 4 Drawing Sheets

Section C-C

Section A-A

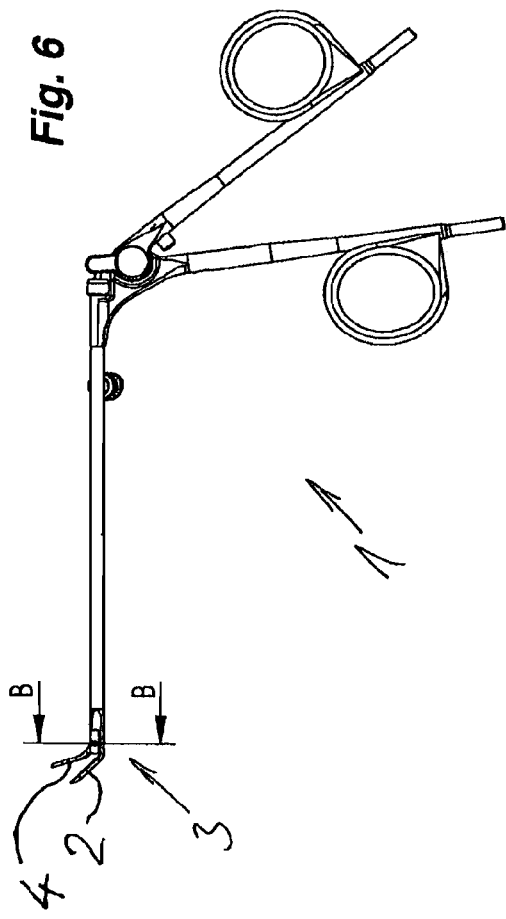
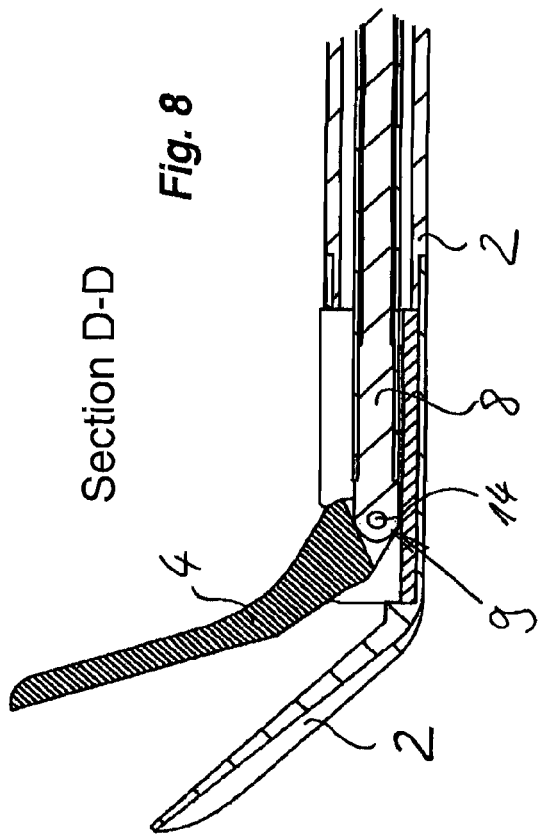
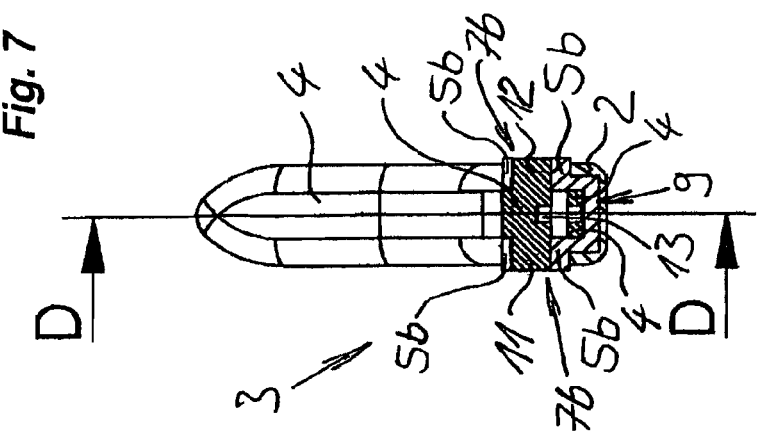

BIPOLAR COAGULATION ELECTRODES

BACKGROUND

The invention relates to a bipolar coagulation forceps with a fixed forceps leg, with a pivot support, and with a forceps leg, which can pivot relative to the fixed forceps leg by means of a pivot element and which is electrically insulated from the fixed forceps leg, with the forceps legs essentially being made from biocompatible metal.

Such coagulation forceps are already known and allow operations to be performed in extremely tight spaces in ear-nose-and-throat medicine, in orthopedics, or in neurosurgery, especially for minimally invasive surgeries. Here, the tissue is grasped and, for example, clamped, cut, or nibbled. Because the coagulation instruments are inserted into the operating space through a comparatively narrow trocar, especially with an inner diameter of approximately 5 mm, or else through operating openings that are as small as possible in the body, the dimensions of the instruments must be minimal accordingly. For better viewing, as a rule, an optical instrument, for example, an endoscope, is also used, which likewise must be inserted in addition to the instrument, and this even further increases the necessity for an instrument with minimal dimensions.

In addition to the reliable electrical insulation of the forceps legs from each other, the stability of the pivot bearing of the forceps legs is also important for a long service life of the instrument. Here, the often installed mechanical overload protection can only insignificantly prolong the service life of the instrument.

SUMMARY

Therefore, there is the objective of providing a bipolar coagulation forceps of the type mentioned in the introduction, for which the required minimal dimensions exhibit high stability, with the stationary forceps leg being electrically insulated from the pivotable forceps leg.

To meet this objective, the invention provides, in particular, that the pivot element is essentially made from biocompatible metal and attaches directly to the moving forceps leg and that, arranged on or fixed to the fixed forceps leg as a pivot support, there is an insulating body, which electrically insulates the pivot element and the moving forceps leg from the fixed forceps leg and on which the moving forceps leg is supported by means of the pivot element. Due to the pivot element being made from metal, this can be dimensioned relatively small and can thus receive high forces. Here, the pivot element is supported on the insulating body and therefore with the pivotable forceps leg electrically insulated from the fixed forceps leg in a simple way. For application in surgery, the use of biocompatible metal is necessary, which can be, in particular, stainless steel, titanium, gold, silver, a noble metal alloy, or a tungsten alloy, chromium alloy, and/or nickel alloy, or a similar hard-metal alloy. Such metals are neither toxic nor do they promote coagulation and also do not trigger allergies or other immunological reactions. In addition, they are not corroded by sterilizing chemicals.

A preferred embodiment of the coagulation forceps according to the invention provides that the pivot element is an axle or shaft, which is preferably supported at its end regions in approximately opposing receiving bearings in the insulating body, and that the pivot element is formed as a continuous, especially one-piece, axle or shaft, whose two end regions are each supported in a receiving support bearing of the insulating body. Such a continuous pivot element can guide the forces acting upon the pivotable forceps leg uniformly into the receiving bearings of the pivot support, wherein simultaneously a large degree of movement can be achieved for the pivotable forceps leg.

Another preferred configuration provides that the pivot element is divided into two parts, which are approximately aligned with each other and which have a spacing between themselves and which are each supported in receiving bearings of the pivot support, and that the receiving bearings have a slot and/or an open spacing between themselves. In the open spacing, which is also provided for the configuration of the pivot element as an axle or shaft between the receiving bearings, in an advantageous way a link element for pivoting the moving forceps leg can be arranged.

Here, it is advantageous if a push/pull rod is provided for pivoting the moving forceps leg and if the link position of the push/pull rod to the moving forceps leg is arranged eccentric to its pivot axis. Through the push/pull rod acting eccentrically on the pivotable forceps leg, its straight line motion can be converted into a rotational or pivoting motion of the forceps leg, with a comparatively low expenditure of force being necessary.

Here, it is especially advantageous if the push/pull rod engages the moving forceps leg in the region of the link positioned at least partially between the parts of the pivot element and between the receiving bearings. Therefore, the link position of the push/pull rod can be arranged for a two-piece pivot element between the two parts of the pivot element especially close to the pivot axis of the pivotable forceps leg, whereby the dimensions of the coagulation forceps can be reduced primarily in the joint region. The closer the link position of the push/pull rod is arranged to the pivot axis of the forceps leg, the more force is needed for moving the push/pull rod and thus for pivoting the forceps leg, but the smaller the dimensions of the link. The position of the link of the push/pull rod can be selected such that comparatively small dimensions in the joint region, as well as sufficiently easy movement of the push/pull rod, and thus of the forceps leg, are possible.

For electrical insulation of the especially metallic push/pull rod from the metallic, fixed forceps leg, it is preferable when the insulating body is formed as a continuous, especially one-piece, body at least in the region between the link position of the push/pull rod and the fixed forceps leg. Because the insulating effect can be maintained even for contact between the push/pull rod and the fixed forceps leg, a possible spark between parts lying very close to each other can also be prevented.

An advantageous configuration of the moving forceps leg according to the invention provides that the end of the moving forceps leg pointing towards the insulating body has two bearing disks spaced apart from each other as a pivot element, that the bearing disks have a diameter that is approximately the same size or larger in comparison with the cross section of the moving forceps leg, and that the bearing disks are supported in the pivot bearings formed in the insulating body. Here, the bearing disks form the pivot elements of the pivotable forceps leg, which are supported in fitted receiving bearings of the insulating body and which together form a pivot joint, which can receive large forces. The push/pull rod can attach directly to a bearing disk or to both bearing disks eccentrically in order to cause the forceps leg to pivot.

An alternative configuration of the moving forceps leg according to the invention provides that the end of the moving forceps leg pointing towards the insulating body has two bearing journals spaced apart from each other as pivot elements, that the bearing journals have a smaller diameter in comparison with the cross section of the moving forceps leg, and that the bearing journals are each supported in a receiving bearing of the pivot support formed in the insulating body. Just like the bearing disks, the bearing journals form the pivot elements of the pivotable forceps leg. The pivoting arrangement formed with the receiving bearings and the bearing journals has comparatively small dimensions.

It is advantageous when the slot or spacing between the pivot elements is approximately aligned with the longitudinal axis of the push/pull rod and that the longitudinal center of the slot or spacing between the pivot elements and the longitudinal center of the open spacing between the receiving bearings of the pivot support, as well as the longitudinal axis of the push/pull rod, run in a common plane, which is arranged perpendicular to the pivot axis of the pivot elements. Therefore, the push/pull rod that can move along its longitudinal axis and the longitudinal axis of the coagulation forceps can engage and attach within this movement at the link position in the free spacing or slot between the receiving bearings of the pivot support extending longitudinally in the same plane as the longitudinal axis of the push/pull rod and if necessary in the slot between the pivot elements likewise running longitudinally in this plane.

For simple assembly of the coagulation forceps according to the invention, it is especially preferable if the pivot element(s) of the moving forceps leg can be plugged or locked or clipped into the receiving bearing of the insulating body.

For the setup of the pivot joint from the smallest possible number of individual parts, especially for simple assembly and also for high strength, it is advantageous if the pivot element(s) of the moving forceps leg are connected integrally to the moving forceps leg. Especially for easy sterilization of the coagulation forceps according to the invention, a simpler mechanical design is preferable so that filigree structures, in which, for example, tissue residue can become caught, can be avoided.

Alternative to the pivot element connected integrally to the moving forceps leg, the pivot element(s) of the moving forceps leg can be connected to the moving forceps leg with a positive or force fit.

For an especially high strength of the joint region, it is advantageous if the insulating body is a metal part electrically insulated from the fixed forceps leg and preferably has a material layer electrically insulating the receiving bearing for the pivot element(s) from the fixed forceps leg. Here, the electrically insulating material layer can be made from plastic or preferably ceramic, in order, as the surface of the receiving bearing, to be stable and resistant to wear for a long time primarily against frictional forces occurring on the receiving bearing.

For an especially good insulating effect, it is preferable when the insulating body is made from electrically insulating material and when the insulating material is preferably ceramic or plastic. In addition to strong insulating properties, ceramic, in particular, exhibits high strength, whereby a large degree of overall stability of the joint region can be achieved.

BRIEF DESCRIPTION OF THE DRAWINGS

Embodiments of the invention are described in more detail below with reference to the drawings. Shown in partially schematized representation are:

FIG. 6 is a side view of another embodiment of the bipolar coagulation forceps according to the invention with forceps legs bent upwards and two bearing journals connected integrally to the pivotable forceps legs as pivot elements, FIG. 7 is a partial section corresponding to the section line B-B in FIG. 6 through the bearing journals and an insulating body supporting these journals, FIG. 8 is a partially cut-away side view corresponding to the section line D-D in FIG. 7.

DETAILED DESCRIPTION OF THE PREFERRED EMBODIMENTS

Figure 1:
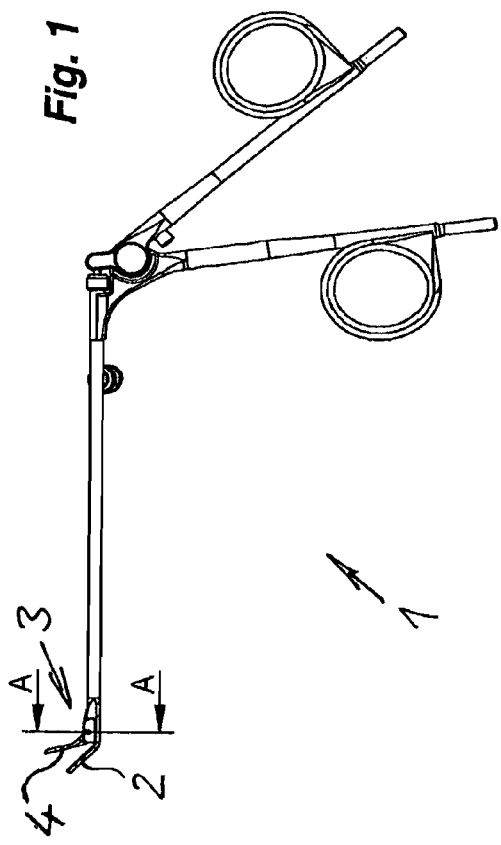
FIG. 1 is a side view of a bipolar coagulation forceps according to the invention with forceps legs bent upwards and a continuous, one-piece axle as pivot element.

A bipolar coagulation forceps designated as a whole with 1 can be recognized in its entirety especially well in FIGS. 1 and 6 and features a fixed forceps leg 2, a pivot support 3, and an electrically insulated forceps leg 4, which can pivot relative to the pivot support 3 by means of a pivot element. The forceps legs 2, 4 are here essentially made from biocompatible metal for high strength and for discharging electrical current to the tissue to be treated.

Figure 2:
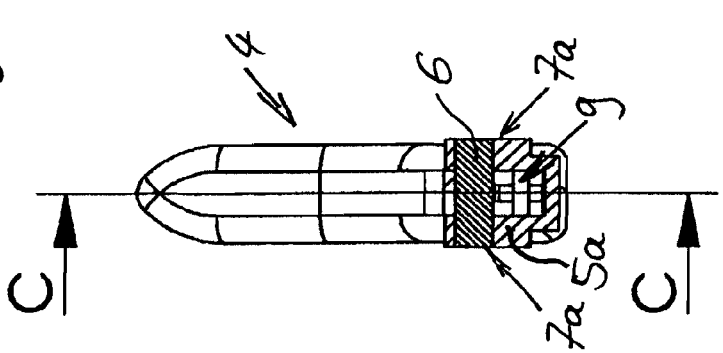
FIG. 2 is a partial section corresponding to section line A-A in FIG. 1 through the pivot element and an insulating body supporting this element.

The pivot element is made from biocompatible metal, likewise for high strength and stability, and attaches directly to the moving forceps leg 4. This is shown particularly clearly in FIGS. 2 and 7. An insulating body 5a, 5b electrically insulating the pivot element and the moving forceps leg 4 from the fixed forceps leg 2 is arranged on the fixed forceps leg 2, with the moving forceps leg 4 being supported on the insulating body 5a, 5b by the pivot element.

In the embodiment shown, the forceps legs 2, 4 have a shape that is bent upwards or at a right angle. However, other shapes, for example, forceps legs extending straight forwards or forceps legs with spoon-like tong parts, are also conceivable and can be combined with each other with the pivot arrangement 3 according to the invention.

Figure 3:
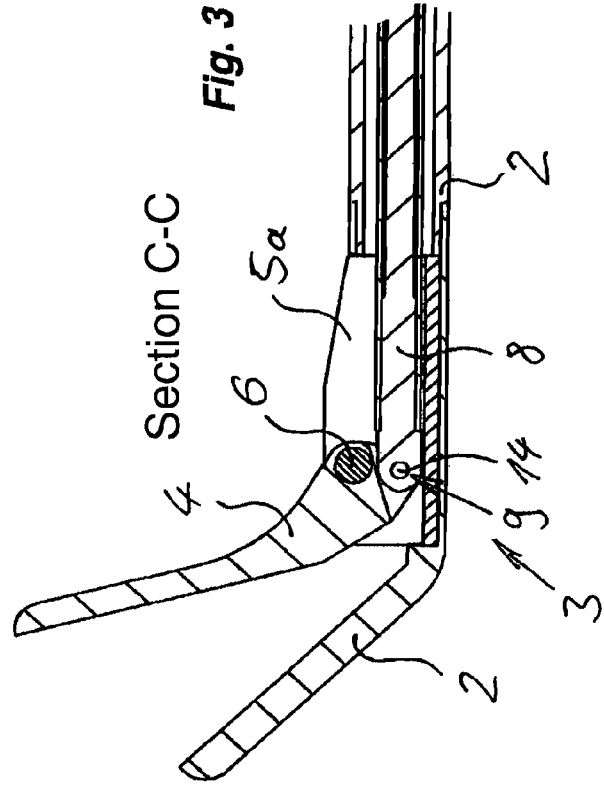
FIG. 3 is a partially cut-away side view corresponding to the section line C-C in FIG. 2.
Figure 4:
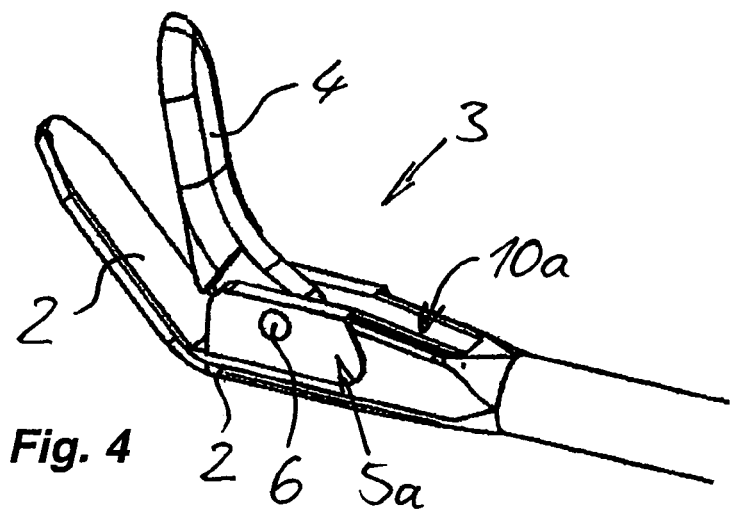
FIG. 4 is a perspective detail view of the opened forceps legs.
Figure 5:
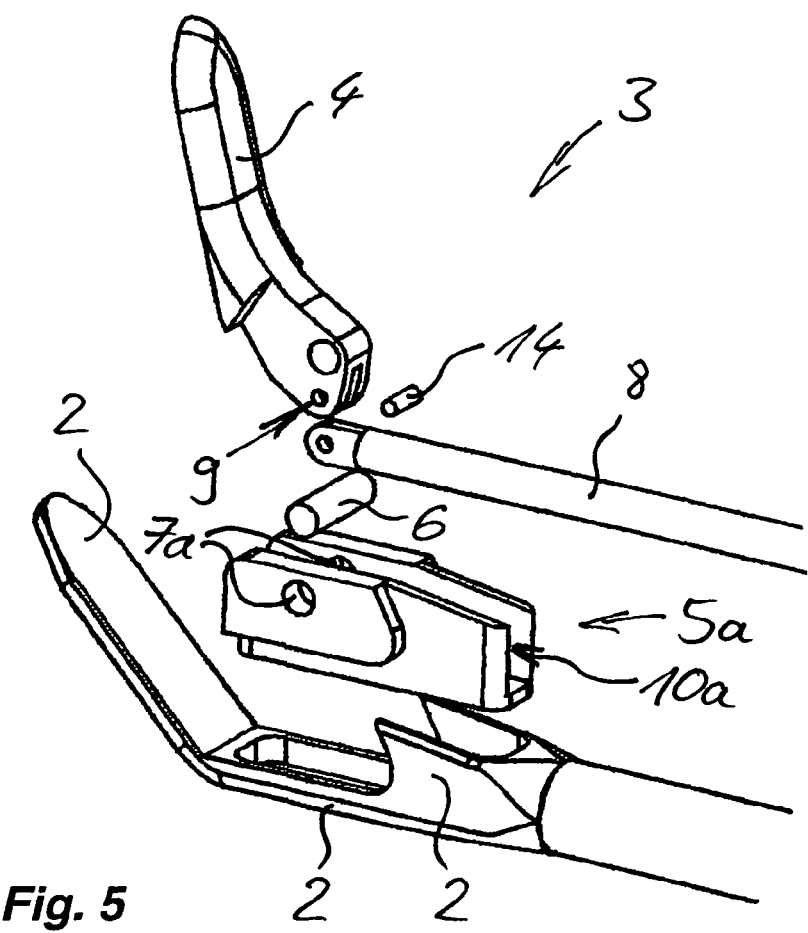
FIG. 5 is an exploded view corresponding to FIG. 4.

In the embodiment of the coagulation forceps 1 according to the invention shown in FIGS. 1 to 5, the pivot element is a one-piece axle 6, which is supported at its end regions in two opposing receiving bearings 7a in the insulating body 5a. In FIGS. 4 and 5, it can be recognized that the diameter of the axle 6 can be even greater than in the shown example according to the requirements for stability of the pivot connection, because sufficient space is available for this purpose on the insulating body 5a and on the moving forceps leg 4. On the other hand, if the requirements for stability of the pivot connection are less, then the dimensions of the insulating body 5a can be further reduced for use of an axle 6 with similar or smaller dimensions as in FIGS. 4 and 5. Therefore, the total diameter of the coagulation forceps 1 can be reduced in this region and thus even better handling, especially better insertability into trocars or narrow operating openings, can be achieved.

The axle 6 is connected directly and with a positive fit to the moving forceps leg 4.

For pivoting the moving forceps leg 4, a push/pull rod 8 is provided, which attaches to the moving forceps leg 4 at a link position 9 arranged eccentrically to the pivot axis of the moving forceps leg 4 and which can be recognized in FIGS. 3 and 5. Here, the push/pull rod 8 is fixed to a link axle 14 at the link position 9. Between the receiving bearings 7a there is an open spacing 10a. The push/pull rod 8, which is located with its longitudinal axis in the same plane as the longitudinal center of the open spacing 10a, passes through this open spacing in the longitudinal direction. Here, the link position 9 and also the longitudinal axis of the push/pull rod 8 are aligned with each other.

As can be recognized in FIG. 5, the insulating body 5a is formed continuous in the region of the link position 9 of the push/pull rod 8 and the fixed forceps leg 2 and as a one-piece part in the shown embodiment, so that the electrical insulation effect is maintained even for contact between the push/pull rod 8 and the fixed forceps leg 2.

FIGS. 6 to 10 show an embodiment, in which the pivot element is divided into two parts that are aligned with each other and is formed as bearing journals 11, 12, which are each supported in a receiving bearing 7b of the insulating body 5b. The bearing journals 11, 12 have a smaller diameter in comparison with the cross section of the moving forceps leg 4 and are connected integrally to the moving forceps leg 4.

Figure 10:
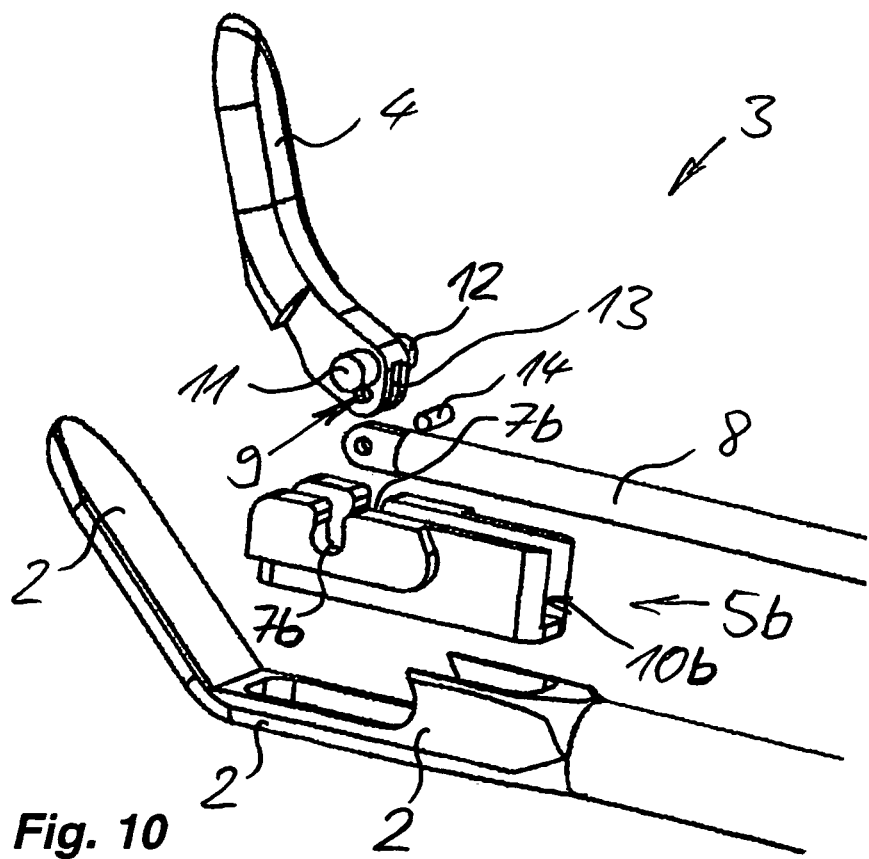
FIG. 10 is an exploded view corresponding to FIG. 9.

As can be recognized in FIG. 10, between the receiving bearings 7b there is an open spacing 10b parallel with its longitudinal axis to the longitudinal axis of the push/pull rod 8. The push/pull rod 8 passes through the open spacing 10b provided in the insulating body 5b in the longitudinal direction and is fixed eccentrically by a link axle 14 to the moving forceps leg 4 at the link position 9 aligned with the longitudinal axis of the push/pull rod 8.

Between the bearing journals 11, 12 there is a slot 13 arranged with its longitudinal center with the longitudinal axis of the push/pull rod 8 in the same plane in the region between the receiving bearings 7b. This slot can be recognized in FIGS. 7 and 10 and the push/pull rod 8 can partially engage in this slot. Therefore, the link position 9 can be arranged closer to the pivot axis of the moving forceps leg 4, whereby the eccentric excursion of the push/pull rod 8 is smaller for the motion of the moving forceps leg 4, so that a reduction of the structural size is achieved in this region.

The partial section in FIG. 7 shows an embodiment of the pivot support 3, in which the bearing journals 11, 12 are connected integrally to the moving forceps leg 4. Corresponding to the section line B-B, in particular the moving forceps leg 4 and the insulating body 5b are partially cut away.

Like in the embodiment with continuous axle 6, also in the configuration with bearing journals 11, 12, the insulating body 5b is formed in one piece in the region between the link position 9 of the push/pull rod 8 and the fixed forceps leg 2, as FIG. 10 also shows.

Figure 9:
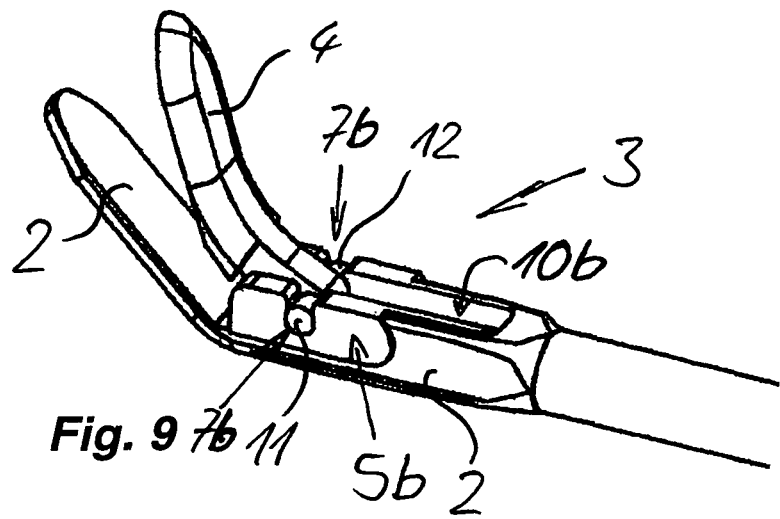
FIG. 9 is a perspective detail view of the opened forceps legs.

As can be recognized in FIGS. 9 and 10, the receiving bearings 7b are formed as a snap-on mechanism. Therefore, for the assembly of the coagulation forceps 1 according to the invention, the bearing journals 11, 12 can be fixed in the receiving bearings 7b by a clip-on motion.

The invention claimed is:

1. Bipolar coagulation forceps (1) comprising a fixed forceps leg (2), with a pivot support (3), having a receiving bearing (7b) with a slot or an open spacing (10b) located therebetween, and with a pivoting forceps leg (4), which can pivot relative to the fixed forceps leg via a pivot element (11, 12) and which is electrically insulated from the fixed forceps leg, the forceps legs (2, 4) being made from biocompatible metal, the pivot element (11, 12) is integral with the pivoting forceps leg (4), comprises two end portions separated by a slot (13) in the pivoting forceps leg (4), and is made from biocompatible metal, the end portions are each supported in the receiving bearing (7b) of the pivot support (3) which is formed as an insulating body (5b) and electrically insulates the pivot element (11, 12) and the moving forceps leg (4) from the fixed forceps leg (2), the insulating body (5b) is arranged on or fixed to the fixed forceps leg (2) as the pivot support (3), on which the moving forceps leg (4) is supported by the pivot element (11, 12) which is clipped into the receiving bearings (7b) of the insulating body (5b).

2. Coagulation forceps according to claim 1, wherein a push/pull rod (8) is provided, that articulates the moving forceps leg (4), a link position (9) of the push/pull rod (8) is arranged on the moving forceps leg (4) eccentric to a pivot axis thereof.

3. Coagulation forceps according to claim 2, wherein the push/pull rod (8) engages in a region of the link position (9) to the moving forceps leg (4) at least partially between parts of the pivot element (11, 12), which are approximately aligned with each other, and between the receiving bearings (7b).

4. Coagulation forceps according to claim 2, wherein the insulating body (5b) is formed in one piece, at least in a region between the link position (9) of the push/pull rod (8) and the fixed forceps leg (2).

5. Coagulation forceps according to claim 2, wherein the slot (13) between the pivot elements (11, 12) is approximately aligned with a longitudinal axis of the push/pull rod (8) and a longitudinal center of the slot (13) between the pivot elements (11, 12) and a longitudinal center of the open spacing (10b) between the receiving bearings (7b) of the pivot support (3), as well as a longitudinal axis of a push/pull rod (8) of the forceps, extend in a common plane, which is arranged perpendicular to a pivot axis of the pivot elements (11, 12).

6. Coagulation forceps according to claim 1, wherein an end of the moving forceps leg (4) pointing towards the insulating body has two bearing disks, spaced apart from each other, as the pivot element, the bearing disks have a diameter that is approximately equal in size or larger in comparison with a cross section of the moving forceps leg (4), and the bearing disks are each supported in a corresponding receiving bearing of the pivot support (3) formed as the insulating body.

7. Coagulation forceps according to claim 1, wherein an end of the moving forceps leg (4) pointing towards the insulating body (5b) has two bearing journals (11, 12) spaced apart from each other as a pivot element, the bearing journals (11, 12) have a smaller diameter in comparison with a cross section of the moving forceps leg (4), and the bearing journals (11, 12) are each supported in one of the receiving bearings (7b) of the pivot support (3) formed as the insulating body (5b).

8. Coagulation forceps according to claim 1, wherein the pivot element (11, 12) of the moving forceps leg (4) is connected with a positive and/or force fit to the moving forceps leg (4).

9. Coagulation forceps according to claim 1, wherein the insulating body is a metal part electrically insulated from the fixed forceps leg (2) and has a material layer electrically insulating the receiving bearings (7b) for the pivot element (11, 12) from the fixed forceps leg (2).

10. Coagulation forceps according to claim 1, wherein the insulating body (5b) is made from electrically insulating material.

11. Coagulation forceps according to claim 10, wherein the insulating material is ceramic or plastic.

12. Bipolar coagulation forceps (1) comprising:
a fixed forceps leg (2), with a pivot support (3);
a pivoting forceps leg (4), which pivots relative to the fixed forceps leg via a pivot element (11, 12) supported in a receiving bearing (7b) of the pivot support (3) and which is formed as an insulating body (5b) and is electrically insulated from the fixed forceps leg, the forceps legs (2, 4) being made from biocompatible metal, the pivot element (11, 12) is made from biocompatible metal and is integral with the moving forceps leg (4) and is clipped into the receiving bearings (7*b*) of the insulating body (5*b*);

a push/pull rod (8), a link position (9) of the push/pull rod (8) is arranged on the moving forceps leg (4) eccentric to a pivot axis thereof; and the insulating body (5*b*) formed in one piece, at least in a region between the link position (9) of the push/pull rod (8) and the fixed forceps leg (2) electrically insulating the pivot element (11, 12) and the moving forceps leg (4) from the fixed forceps leg (2), which is arranged on or fixed to the fixed forceps leg (2) as a pivot support (3), on which the moving forceps leg (4) is supported by the pivot element (11, 12).

* * * * *